US010136876B2

(12) United States Patent
Guzina et al.

(10) Patent No.: US 10,136,876 B2
(45) Date of Patent: Nov. 27, 2018

(54) SYSTEM AND METHOD FOR LOCAL ESTIMATION OF NONLINEAR TISSUE ELASTICITY WITH ACOUSTIC RADIATION FORCE

(71) Applicant: Mayo Foundation for Medical Education and Research, Rochester, MN (US)

(72) Inventors: Bojan Guzina, Minneapolis, MN (US); Egor Dontsov, Minneapolis, MN (US); Mostafa Fatemi, Rochester, MN (US)

(73) Assignees: MAYO FOUNDATION FOR MEDICAL EDUCATION AND RESEARCH, Rochester, MN (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 922 days.

(21) Appl. No.: 14/038,181

(22) Filed: Sep. 26, 2013

(65) Prior Publication Data
US 2014/0088421 A1 Mar. 27, 2014

Related U.S. Application Data

(60) Provisional application No. 61/706,442, filed on Sep. 27, 2012.

(51) Int. Cl.
*A61B 8/08* (2006.01)

(52) U.S. Cl.
CPC .............. *A61B 8/485* (2013.01); *A61B 8/085* (2013.01)

(58) Field of Classification Search
CPC .................................. A61B 8/485; A61B 8/08
See application file for complete search history.

(56) References Cited

U.S. PATENT DOCUMENTS 5,903,516 A 5/1999 Greenleaf et al.

OTHER PUBLICATIONS

Catheline, et al., Measurement of Elastic Nonlinearity of Soft Solid with Transient Elastography, Journal of the Acoustical Society of America, 2003, 114(6)(Pt.1):3087-3091.
Dontsov, et al., Effect of Low-Frequency Modulation on the Acoustic Radiation Force in Newtonian Fluids, SIAM J. Appl. Math., 2011, 71(1):356-378.
Dontsov, et al., Acoustic Radiation Force in Tissue-Like Solids Due to Modulated Sound Field, Journal of the Mechanics and Physics of Solids, 2012, 60:1791-1813.

(Continued)

*Primary Examiner* — Hien Nguyen
(74) *Attorney, Agent, or Firm* — Yakov S. Sidorin; Quarles & Brady LLP (57) ABSTRACT

Ultrasound system and method configured to locally determine a parameter of nonlinear tissue elasticity by monitoring shear wave propagating through the tissue. The shear wave is caused by an acoustic radiation force (ARF) which is applied to the tissue by ultrasound irradiation locally, in a focal region of the ultrasound beam and which is a function of the intensity of ultrasound irradiation, its time rate, and the featured nonlinearity parameter. The irradiation does not involve a quasi-static compression of the tissue, thereby permitting local estimation of nonlinear tissue elasticity and circumventing the need to solve the global inverse problem.

9 Claims, 5 Drawing Sheets

(56) References Cited

OTHER PUBLICATIONS

Hachemi, et al., Transient Displacement Induced in Shear Wave Elastography: Comparison Between Analytical Results and Ultrasound Measurements, Ultrasonics, 2006, 44:e221-e225.

Lake, et al., Tensile Properties and Fiber Alignment of Human Supraspinatus Tendon in the Transverse Direction Demonstrate Inhomogeneity, Nonlinearity, and Regional Isotropy, Journal of Biomechanics, 2010, 43:727-732.

Oberai, et al., Linear and Nonlinear Elasticity Imaging of Soft Tissue In Vivo: Demonstration of Feasibility, Phys. Med. Biol., 2009, 54(5):1191-1207.

Sarvazyan, et al., Shear Wave Elasticity Imaging: A New Ultrasonic Technology of Medical Diagnostics, Ultrasound in Med. & Biol., 1998, 24(9):1419-1435.

SYSTEM AND METHOD FOR LOCAL ESTIMATION OF NONLINEAR TISSUE ELASTICITY WITH ACOUSTIC RADIATION FORCE

CROSS-REFERENCE TO RELATED APPLICATIONS

The present application relates to the U.S. Provisional Patent Application No. 61/706,442 filed on Sep. 27, 2012 and titled "System and Method for Local Estimation of Nonlinear Tissue Elasticity with Acoustic Radiation Force." The disclosure of the above-mentioned provisional application is incorporated herein by reference in its entirety.

TECHNICAL FIELD

The invention relates to propagation of acoustic waves in a deformable medium and, more particularly, to system and method for local estimation of a nonlinear elastic parameter characterizing such medium with the use of an ultrasound system.

SUMMARY

Embodiments of the present invention provide a method for locally determining a nonlinear elastic parameter (interchangeably referred to as the nonlinearity parameter, nonlinearity coefficient) of a subject with an ultrasound system. The method includes detecting ultrasound energy reflected from at least two detection points of the subject by irradiating these at least two detection points with a second ultrasound wavefront. The method further includes determining, from said detected ultrasound energy, echo data indicative of a target shear wave induced in the subject locally, at an origin region, by a target acoustic radiation force that formed with irradiating the origin region with a first ultrasound wavefront generated by said ultrasound system. Such target acoustic radiation force has a component that is non-linear with respect to an amplitude of the first ultrasound wavefront. The target shear wave propagates from the origin region towards the at least two detection points. In addition, the method includes determining, from the echo data, target parameters of the target shear wave, which target parameters include at least one of speed and attenuation of the target shear wave; and calculating normalized parameters of a normalized shear wave induced in the subject locally, at the origin region, by a normalized acoustic radiation force formed with irradiating the origin region with said first ultrasound wavefront under normalization conditions; and computing a mean ratio of said target and normalized parameters. The normalization conditions are defined by such a product of a peak value of intensity of said first ultrasound wavefront and the nonlinearity parameter that is substantially equal to one.

In one implementation, at least one of the first and second ultrasound wavefronts is defined by one or more of an amplitude-modulated ultrasound beam and a plurality of ultrasound beams having different frequencies. Such ultrasound beams may be, for example, concentric. The first ultrasound wavefront may be defined by a first substantially focused amplitude-modulated ultrasound beam, and the origin region may be substantially coextensive with a focal region of this first beam. In one embodiment, the calculation of normalized parameters includes computing a normalized displacement field caused in the subject by the normalized acoustic radiation force, which computing is carried out with the use of an one or more of an analytical approximation and an elastodynamic Green's function. Alternatively or in addition, the method may further comprise determining, from the computed mean ratio, a relative nonlinearity coefficient characterizing the origin region.

Embodiments further provide an ultrasound system configured for determination of a material nonlinearity of a subject. The system includes an ultrasound transducer configured to generate an ultrasound wavefront defining a focal region in the subject and to receive echo data indicative of an acoustic radiation force formed in the focal region in response to irradiating said focal region with the ultrasound wavefront, such that the acoustic radiation force has a component that is non-linear with respect to intensity of the first ultrasound wavefront and that defines a shear wave propagating from the focal region outwardly. The system additionally includes a computer-readable tangible non-transitory medium with a computer program product stored thereon which, when loaded on a data-processing electronic circuitry that is in operable communication with said ultrasound transducer, causes the data-processing electronic circuitry to (i) determine, from the echo data, target parameters of a target shear wave defined in the subject by the acoustic radiation force, such that the target parameters include at least one of speed and attenuation of said target shear wave; and (ii) calculate normalized parameters of a normalized shear wave induced in the subject by a normalized acoustic radiation force that is formed in the focal region by irradiating the focal region with the ultrasound wavefront under normalization conditions; and (iii) computing a mean ratio of said target and normalized parameters.

The normalization conditions are defined by such a product of a peak value of intensity of the ultrasound wavefront and the nonlinearity parameter that is substantially equal to one. In one embodiment, the first ultrasound wavefront is defined by one or more of an amplitude-modulated ultrasound beam and a plurality of ultrasound beams having different frequencies. In a related embodiment, the computer program product further causes said data-processing electronic circuitry to determine, from the computed mean ratio, a relative nonlinearity coefficient characterizing the focal region of the subject.

DETAILED DESCRIPTION

Acoustic radiation force (or ARF) is a physical phenomenon associated with the propagation of acoustic waves in a deformable medium; in biomedical applications, the ARF is often attributed to the presence of attenuation in the medium (which attenuation includes both scattering and absorption of the ultrasound wave; in soft tissues it is dominated by absorption). In essence, the ARF originates from the non-linear terms in the balance of linear momentum governing the propagation of acoustic waves, resulting in the mean motion of the medium under prescribed (zero-mean) ultrasound excitation. In other words, a transfer of momentum occurs in the direction of wave propagation, which generates a force causing displacement of the tissue (on a time-scale slower than that of the ultrasound wave propagation). For example, a high-intensity ultrasound beam applied to the tissue produces substantially constant average ARF. The magnitude, location, spatial extent, and duration of acoustic radiation force can be controlled to interrogate the mechanical properties of the tissue. Acoustic radiation force is being utilized in medical ultrasonic imaging to generate images based on the mechanical properties of the tissue. The imaging modalities include, for example, Acoustic Radiation Force Impulse (ARFI) Imaging, Shear-wave Dispersion Ultrasound Vibrometry (SDUV), Harmonic Motion Imaging (HMI), Supersonic Shear Imaging (SSI), Spatially Modulated Ultrasound Radiation Force (SMURF), and Shear Wave Elasticity Imaging (SWEI). Generally, the force exerted on the medium is evaluated by integrating the acoustic radiation body force (due to the presence of the sonic wave) over the volume of interest (for example over the focal region).

The ARF may be used to facilitate tissue elasticity imaging (via, for example, non-invasive palpation). To compute this effective force, one needs to average all quadratic terms in the balance of linear momentum over the period of sound vibrations.

Without exception, all of the aforementioned techniques provide for local diagnosis of the tissue by assessing linear elastic parameters of the tissue (such as the speed of the shear wave, for example). The estimation of the tissue's nonlinear elastic parameters is expected to facilitate a differentiation between the malignant lesions and benign lesions in the tissue. See, for example, Oberai et al., "Linear and nonlinear elasticity imaging of soft tissue in vivo: demonstration of feasibility" (*Phys. Med. Biol.,* 54:1191; 2009). Unfortunately, the methodologies that have a capacity to facilitate such estimation entail quasi-static compression of the tissue with the use of an ultrasound beam (from the transducer) for monitoring tissue deformation and, in addition, invariably entail the solution of the global inverse problem that is both computationally expensive and difficult to solve.

Accordingly, the proposed diagnostic method and system combines the advantages of i) using the ARF in terms of local tissue characterization (that is substantially co-extensive with the focal region), and ii) the capability of assessing the nonlinear tissue elasticity for differential cancer diagnosis.

When the amplitude of the ultrasound source is modulated, the ARF becomes modulated too, which provides a possibility of using the ARF for dynamic (as opposed to static) internal palpation in medical diagnosis. The problem with the use of modulated ultrasound is known to be the lack of response to the usual (time-averaging) asymptotic treatment due to the fact that the mean acoustic quantities, computed as the averages over the period of sound vibrations, retain the rapid oscillation features of such vibrations.

To deal with the problem, and according to an embodiment of the invention, the theoretical treatment is pursued via a scaling approach that splits the temporal variable into its "fast" and "slow" components, permitting one to track the contribution of time-harmonic ultrasound and its modulation separately in the solution. By using the concept of "fast" time averaging, it can be shown that the ARF caused by the modulated ultrasound beam is given by $$ARF = C\left(\frac{2\alpha I}{c} + \frac{1}{c^2}\frac{\partial I}{\partial t}\right) \qquad \text{Eq. (1)}$$

where I signifies the intensity of the ultrasound field; a is the tissue's attenuation coefficient; c is the sound speed, and C is the dimensionless parameter of constitutive nonlinearity for a soft tissue (in fluids, C theoretically equals unity). The above-proposed dependency of the ARF considers nonlinear coupling between shear and compressive motions via the presence of parameter C; the term in parentheses has been verified in a one-dimensional setting via an independent finite-difference solution.

Figure 1:
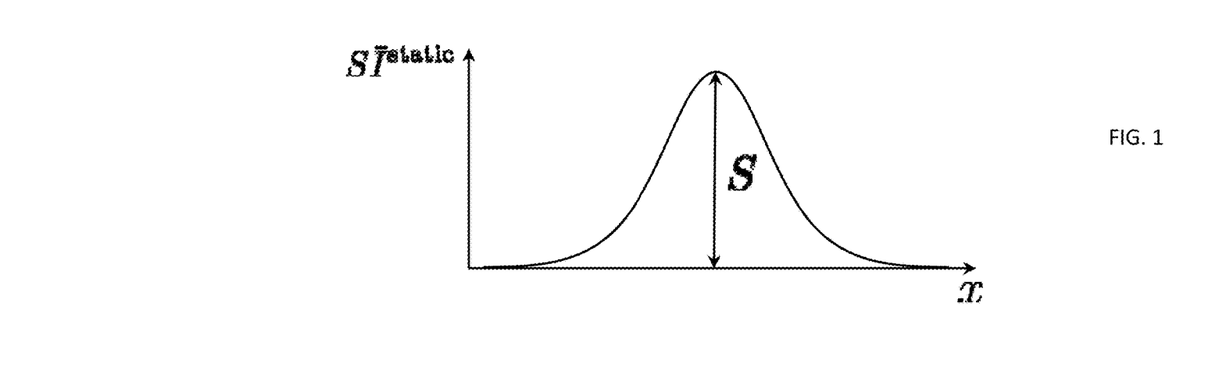
FIG. 1 is a graph illustrating distribution of intensity of a non-modulated ultrasound beam along a transducer-tissue interface.

In Eq. (1), $$I = S \text{ Istatic } M^2(t-z/c) \qquad \text{Eq. (2)}$$

is the intensity of the modulated ultrasound beam, where M is the modulation envelope of the original ultrasound signal, Istatic is the normalized intensity field of the corresponding non-modulated beam, S signifies the peak value of the intensity at the transducers' boundary as shown in FIG. 1, and z is the spatial coordinate along transducer's axis. In comparison, the currently used model for ARF, according to which $$ARF = \frac{2\alpha I}{c} \qquad \text{Eq. (3)}$$

and $$I = S \text{ Istatic } M^2(t) \qquad \text{Eq. (4)},$$

does not take into consideration neither the coupling between shear and compression components for diagnostic purposes, nor the effects of ultrasound modulation that is normally deployed in ARF-based imaging modalities.

In contradistinction with the currently used value of one, compare Eqs. (1) and (3), the nonlinearity parameter C of tissue-mimicking phantoms can be shown to assume values in the range from approximately 7 to approximately 24. This can be confirmed with the use of results presented by Catheline et al. in "Measurement of elastic nonlinearity of soft solid with transient elastography" (*J. Acoust. Soc. Am.,* 114:3087, 2003). Accordingly, the presently used model of Eq. (3) may underestimate the ARF by up to an order of magnitude. Earlier experimental observations by Sarvazyan et al., in "Shear wave elasticity imaging: A new ultrasonic technology of medical diagnostics" (*Ultrasound Med. Biol.,* 24:1419; 1998) support such conclusion.

Figure 2:
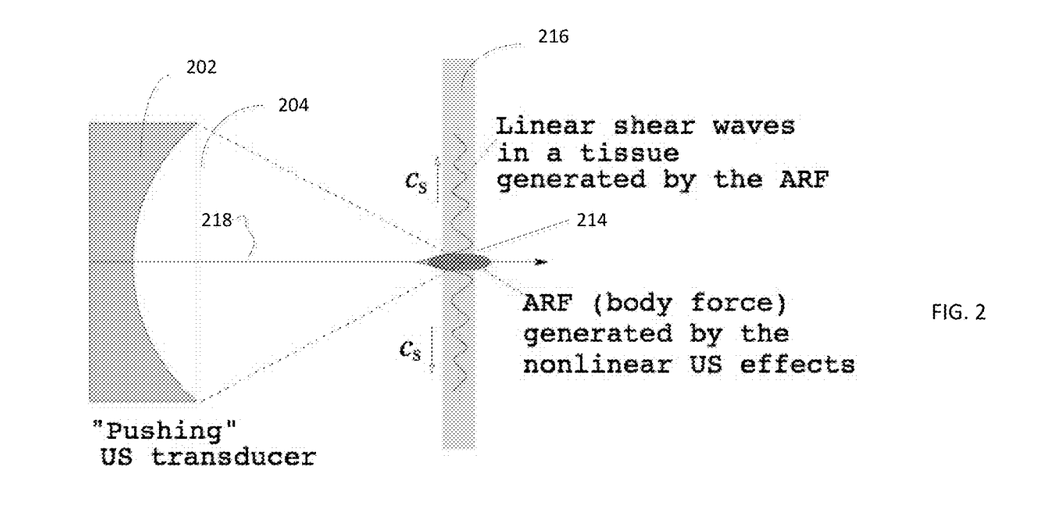
FIG. 2 is a diagram illustrating testing configuration for estimating the tissue's nonlinearity parameter via the acoustic radiation force.

An embodiment of the invention implements a technique for the local estimation of tissue nonlinearity parameter C with the use of ARF determined according to Eqs. (1) and (2). With reference to FIG. 2, a high-intensity, substantially focused ultrasound field 202 is created by a "pushing" ultrasound (US) transducer 204. In this setting, the ARF is generated in a tissue locally via nonlinear ultrasound-tissue interaction within the cigar-shaped focal region 214 (the dimensions of which are generally on the order of few millimeters). Due to this body force, linear shear waves are induced in a tissue within a disc-shaped tissue region 216

(indicated in the FIG. 2 by a shaded rectangular area) that is perpendicular to the transducer's axis 218.

Figure 3A:
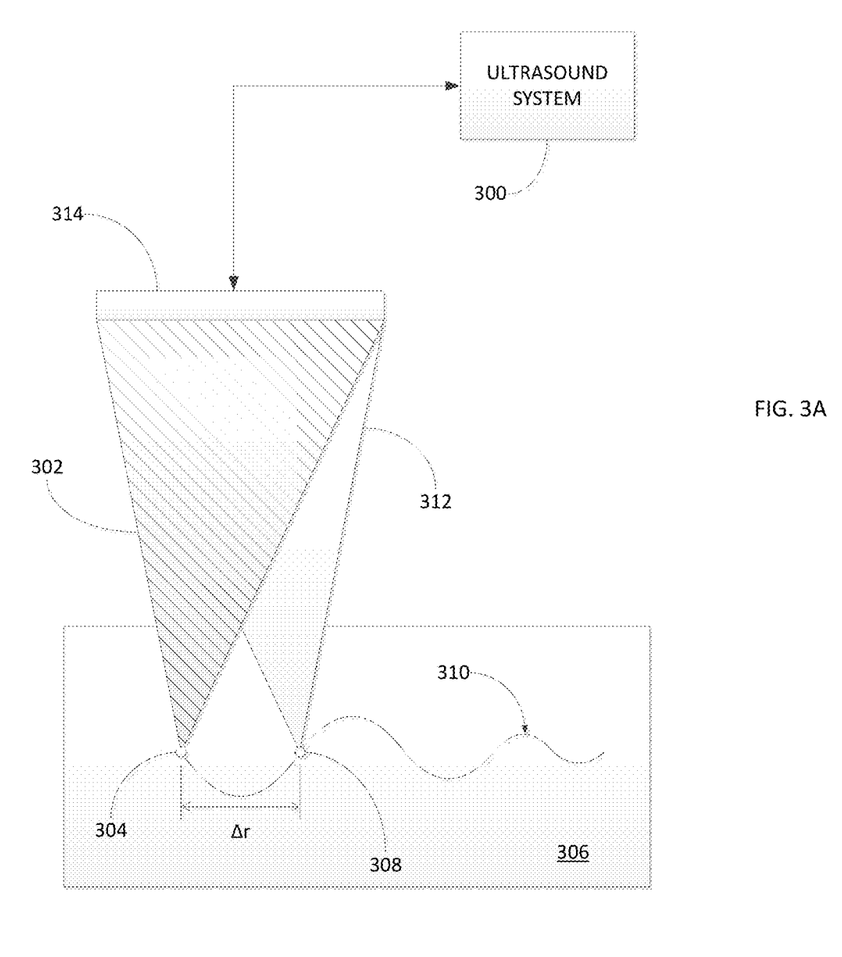
FIG. 3A is block diagram of a shear wave dispersion ultrasound vibrometry ("SDUV") system that can be used with the present invention.

To illustrate one ultrasound system employing the ARF, FIG. 3A provides a diagram of a shear wave dispersion ultrasound vibrometry ("SDUV") system that includes an ultrasonic transducer 314 operable to form focused ultrasound beams. In particular, the transducer 314, such as a linear array transducer, intermittently transmits a beam of ultrasonic vibration pulses 302 to a vibration origin 304 in the tissue of interest 306 to vibrate, or oscillate, subject tissue 306 at a prescribed frequency. When the vibration pulses are not being applied to the subject 306, the focus of the transducer may be electronically steered to a motion detection point 308 at a distance, Δr, from the vibration origin 304 and vibratory motion 310 at that point is detected by applying interrogating ultrasonic detection pulses 312 at that point. Under the direction of a digital controller of the ultrasound system 300 (which controls the transmission and reception of signals), a vibration mode may be multiplexed with a detection mode. This enables the detection of the vibratory motion 310 by the same transducer 314, and, as a result, both vibration of the tissue and detection of such vibration can be achieved without mechanically moving the transducer 314.

Figure 3B:
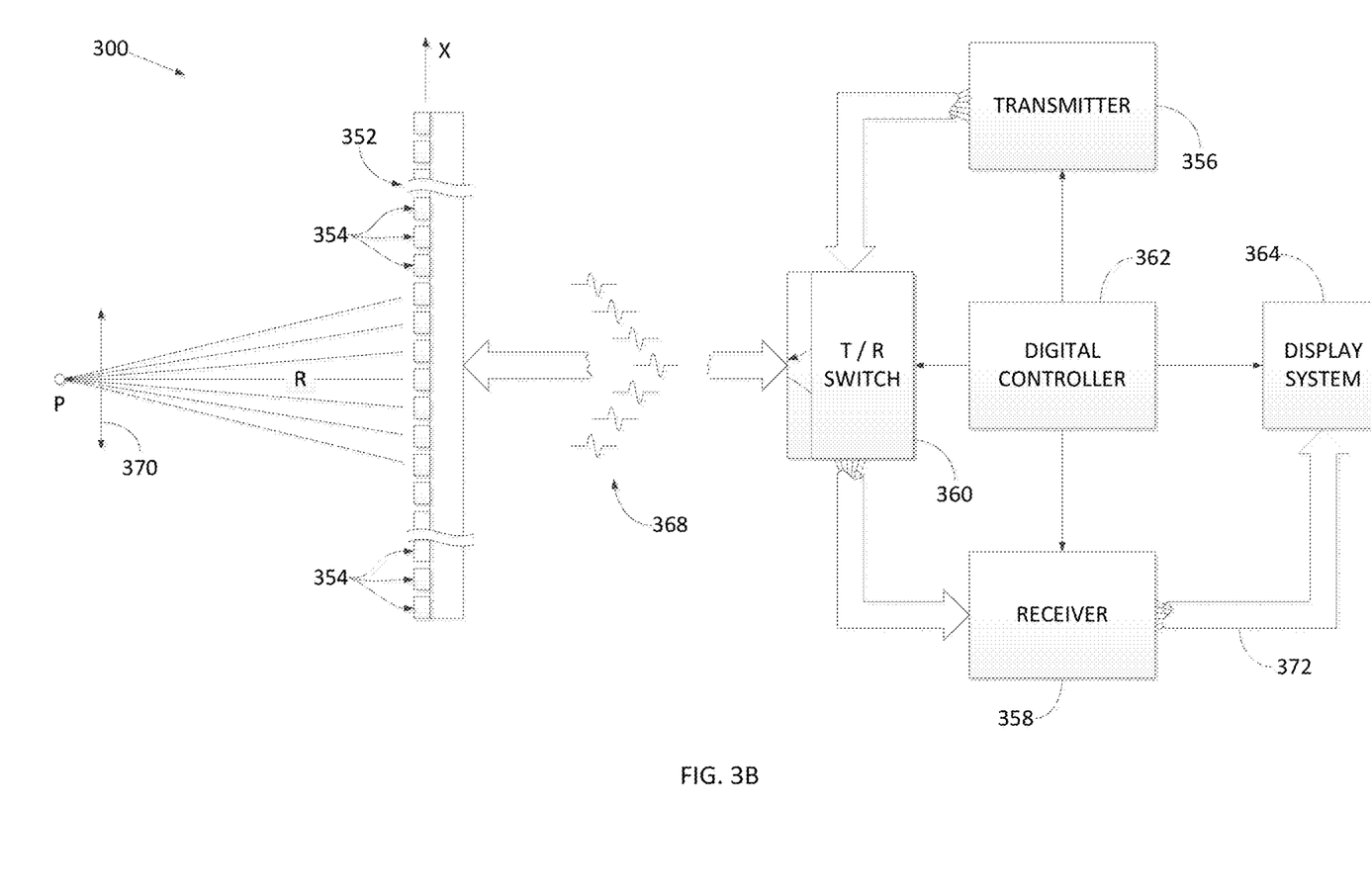
FIG. 3B is a block diagram of an ultrasound system used in the SDUV system of FIG. 3A.

Referring next to FIG. 3B, an ultrasonic imaging system 300, which forms a part of the SDUV system of FIG. 3A, includes a transducer array 352 containing a plurality of separately driven elements 354 that each produce a burst of ultrasonic energy when energized by a pulse produced by a transmitter 356. The ultrasonic energy reflected back to the transducer array 352 from the tissue of interest is converted to an electrical signal by each transducer element 354 and applied separately to a receiver 358 through a set of switches 360. The transmitter 356, receiver 358, and the switches 360 are operated under the control of a digital controller 362 responsive to the commands input by the human operator. A complete scan is performed by acquiring a series of echoes in which the switches 360 are set to their transmit position, the transmitter 356 is gated on momentarily to energize each transducer element 354, the switches 360 are then set to their receive position, and the subsequent echo signals produced by each transducer element 354 are applied to the receiver 358. The separate echo signals from each transducer element 354 are combined in the receiver 358 to produce a single echo signal which is employed to produce a line in an image on a display system 364.

The transmitter 356 drives the transducer array 352 such that an ultrasonic beam is produced which is directed substantially perpendicular to its front surface. To focus this beam at a range, R, from the transducer 352 a subgroup of the elements 354 are energized to produce the beam, and the pulsing of the inner elements 354 in this subgroup are delayed relative to the outer elements 354 as shown at 368. A beam focused at a region P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 304. In this manner a single scan line in the image is formed.

To generate the next scan line, the subgroup of elements to be energized are shifted one element position along the transducer length and another scan line is required. As indicated by the arrow 370, the focal region P of the ultrasonic beam is thus shifted along the length of the transducer 352 by repeatedly shifting the location of the energized subgroup of elements 354.

Figure 3C:
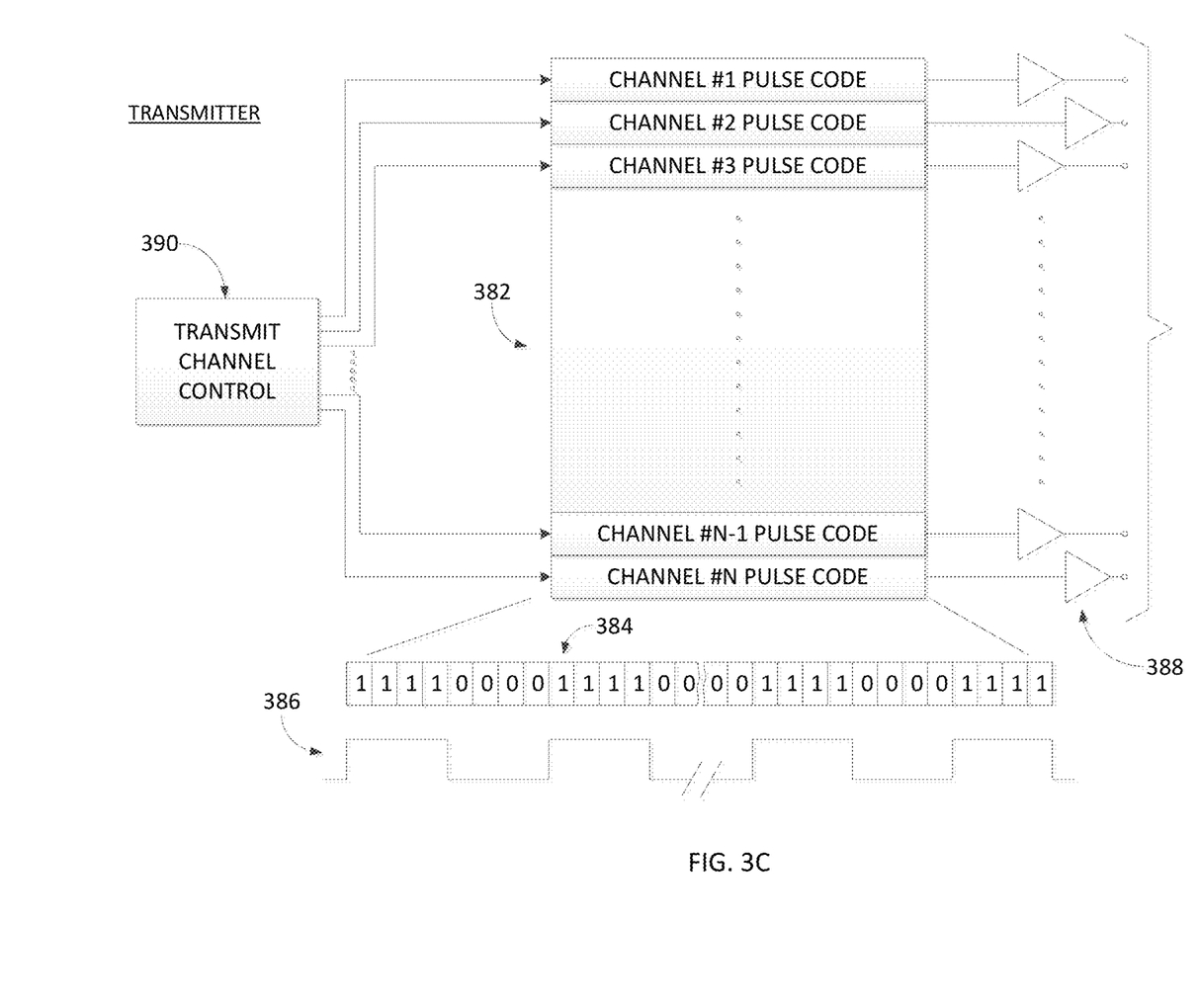
FIG. 3C is a block diagram of a transmitter which forms part of the ultrasound system of FIG. 3A

Referring now to FIG. 3C, the transmitter 356 includes a set of channel pulse code memories which are indicated collectively at 382. Each pulse code memory 382 stores a bit pattern 384 determining the frequency of the ultrasonic pulses 386 that is to be produced. This bit pattern is read out of each pulse code memory 382 by a master clock and applied to a driver 388 which amplifies the signal to a power level suitable for driving the transducer 382. In the example shown in FIG. 3C, the bit pattern is a sequence of four "1" bits alternated with four "0" bits to produce a 5 MHz ultrasonic pulse 386. The transducer elements 384 to which these ultrasonic pulses 386 are applied respond by producing ultrasonic energy.

If steering of the transmitted beam of the ultrasound energy in the desired manner is required, the pulses 386 for each of the channels can be produced and appropriately delayed. These delays are provided by a transmit control 390 which receives control signals from the digital controller 362. When the control signal is received, the transmit control 390 gates a clock signal through to the first transmit channel 382. At each successive delay time interval thereafter, the clock signal is gated through to the next channel pulse code memory 382 until all the channels to be energized are producing their ultrasonic pulses 386. Each transmit channel 382 is reset after its entire bit pattern 384 has been transmitted and the transmitter 356 then waits for the next control signal from the digital controller 362. Referring again to FIG. 3B, by operating the transmitter 356 in the above-described manner, the ultrasound energy can be focused at the focal region P. This focal point can be steered electronically with the appropriate changes to the timing delays provided by the transmit control 390. The terms "focal point" and "focal region" as referred to herein, includes not only a single point object in the usual sense, but also a general region-of-interest to which ultrasound energy is delivered in a substantially focused manner.

Figure 4:
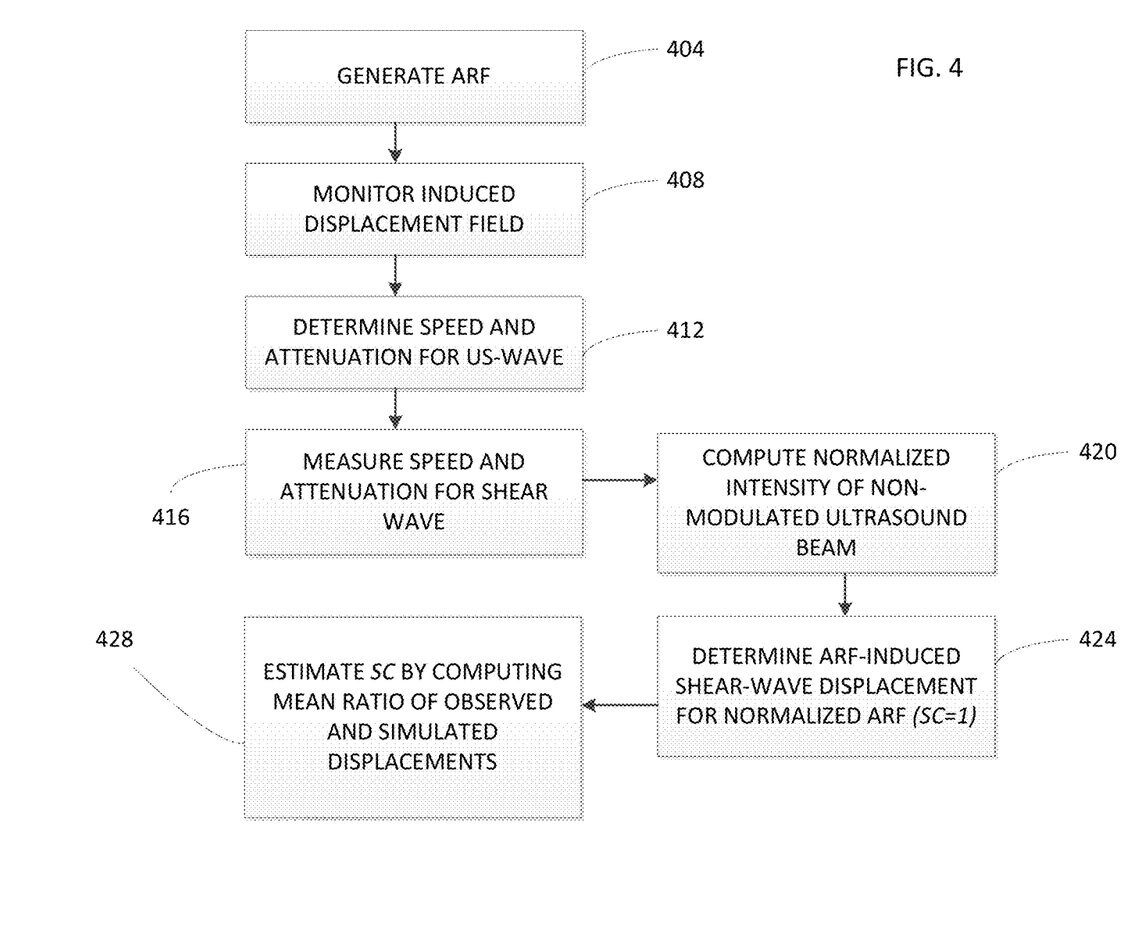
FIG. 4 is a diagram representing embodiment of a method for the local estimation of tissue's nonlinearity parameter C.

Referring again to the setting of FIGS. 2 and 3B and with the reference to the diagram in FIG. 4, the value of C within the focal region (214, P) is estimated, according to an embodiment of the invention, with a method including:

Generating, at step 404, a modulated ARF in the tissue of interest by way of amplitude-modulated ultrasound beam (or, alternatively or in addition, with dual or multiple ultrasound beams characterized by different frequencies, or by any other suitable means);

Monitoring and/or detecting, at step 408, the shear-wave displacement field $u^{obs}(x_k, x_0)$ corresponding to propagation of the (ARF-induced) linear shear waves in the tissue at hand with the use of the same or, alternatively, a separate "sensing" US transducer array (for example, with the use of the monitoring techniques such as pulse-echo, Flash imaging, echo correlation);

Determining or estimating the mass density $\rho$, the ultrasound wave speed c in the tissue, as well as the ultrasound attenuation coefficient $\alpha$ at step 412. For example, the mass density and sound speed can be taken respectively as $\rho=1000$ kg/m$^3$ and c=1500 m/sec (or be obtained from independent measurements, or from the published data for a given tissue type). The value of the ultrasound speed varies by less than about 1% in soft tissues. Similarly, the value of the attenuation coefficient can be either measured or assumed from the data characterizing a given tissue type. With reference to Eq. (1), it is noted that at higher modulation frequencies, the second term dominates the expression for the ARF, whereby an accurate estimation of α may not be essential for the success of the proposed technique;

Measuring the shear-wave speed ($c_s$) and shear-wave attenuation ($\alpha_s$), at step 416. This can be accomplished in a variety of ways, for example by extracting the phase delay and amplitude decay information from the shear-wave motion captured at step 408. The measurement of the shear wave speed and attenuation is preferably done by a method employing the use of ultrasound; however other measuring techniques, such as MRI-based and optical-based techniques may be used as well;

Computing the normalized (non-modulated) intensity distribution Istatic, featured in Eq. (2), by any suitable numerical technique (for example, with the use of the angular spectrum method or Rayleigh integral) or by employing an analytical approximation, at step 420;

Performing visco-elastodynamic simulation of the shear wave motion, at step 424 with the use of the body force (ARF) distribution according to Eqs. (1) and (2) with C=1, S=1, and adopting other relevant parameters from the previous steps 404, 408, 412, 416, 420 (namely mass density ρ, ultrasound speed c, attenuation coefficient α, shear wave speed $c_s$ and shear-wave attenuation $\alpha_s$). For example, the simulation of the shear wave motion can be performed with the use of the finite element analysis or any other relevant numerical technique. In addition, the approximate analytical formulae can be used instead of numerical calculations. A computationally faster alternative for time-harmonic modulations is to use elastodynamic Green's function for an infinite (or half-space) viscoelastic solid. In the latter case, the normalized displacement field is computed as $$\bar{u}^{sim}(x,x_0) = \int_D \mathcal{G}(x-y)\overline{ARF}(y,x_0)dy \qquad \text{Eq. (5)}$$

where $\overline{ARF}(y,x_0)$ is the normalized radiation force evaluated at point y with $x_0$ being the position of the focal point of the transducer, G is the elastodynamic Green's function, and the ∈ volume integral is computed over the focal region D;

Computing, at step 428, the mean ratio of the value(s) corresponding to the shear-wave displacement observations and their normalized simulations, obtained previously, as $$SC(x_0) = \frac{1}{n}\sum_{k=1}^{n}\frac{|u^{obs}(x_k,x_0)|}{|\bar{u}^{sim}(x_k,x_0)|} \qquad \text{Eq. (6)}$$

where $|u^{obs}(x_k, x_0)|$ is the measured peak displacement at measurement point $x_k$, and $|\bar{u}_{sim}(x_k,x_0)|$ is the corresponding elastodynamic simulation. The variable $x_0$ denotes simultaneously the position of the focal region (or point) and the point in a tissue where the nonlinearity parameter C is evaluated and k and n are integer variables over which an operation of summation is being performed. In situations where the peak input intensity, S, along transducer-tissue interface is known, the nonlinearity parameter is computable directly from Eq. (6). If S is not available, on the other hand, the product S C can be used to expose the relative nonlinearity coefficient over the region of interest (assuming that S remains a constant value).

To the best of knowledge of related art available to the inventors, such related art does not disclose an approach for estimating the parameter of nonlinear tissue elasticity locally with the use of the ARF. Any method for estimation of C via the existing schemes entails both major 3D simulation of the shear waves for a (global) problem specific to the type of tissue involved (for example, a bodily organ) as well as significant uncertainties stemming from solving the global inverse computational problem.

The effect of applying a modulated ultrasound beam on internal tissue palpation is that the modulated beam constrains i.e. localizes the ARF-induced tissue motion to the neighborhood of the focal region of the beam. Due to the combined effect of inertia and tissue attenuation, there exist correlation between the modulation frequency of an irradiating ultrasound beam and a degree of localization of the tissue response to such beam. In general, the higher the modulation frequency, the more localized tissue response. This localization phenomenon becomes advantageous when imaging a highly heterogeneous tissue, as the localization allows the user to distinguish, in terms of tissue's linear and nonlinear responses, between neighboring tissue regions with high spatial resolution.

The following notes are in order. References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. It is understood that in the drawings, the depicted structural elements are generally not to scale, and certain components may be enlarged relative to the other components for purposes of emphasis and clarity of understanding. It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, in the schematic logical flow chart diagram the depicted order and labeled steps of the logical flow are indicative of one embodiment of the presented method. Other steps and methods may be conceived that are equivalent in function, logic, or effect to one or more steps, or portions thereof, of the illustrated method.

The invention as recited in claims appended to this disclosure is intended to be assessed in light of the disclosure as a whole, including features disclosed in prior art to which reference is made.

An embodiment of the method of the invention is advantageous in that it facilitates determination of the nonlinear elasticity characteristic locally, without a need to take into account the mechanical properties of the entire tissue (an entire bodily organ, for example) and frequently uncertain associated boundary conditions. The proposed methodology allows the user, with the use of the modulation term in Eq. (1), to diminish the effect of ultrasound attenuation α (which may be arduous to measure) on the ARF.

The present invention has been described in terms of one or more preferred embodiments, and it should be appreciated that many equivalents, alternatives, variations, and modifications, aside from those expressly stated, are possible and within the scope of the invention.

What is claimed is:

1. A method for forming an image representing a locally determined nonlinear elastic parameter of a subject with an ultrasound system, the method comprising:
   a) irradiating the subject with a first ultrasound beam generated by a transducer of the ultrasound system to form a target acoustic radiation force in an origin region of the subject,
      wherein the target radiation force has a component that is non-linear with respect to an amplitude of said first ultrasound beam;
   b) transforming said first ultrasound beam into a second ultrasound beam generated by said transducer and focused at a detection point of the subject, said detection point being spatially separated from the origin region in a direction transverse to the first ultrasound beam;
   c) with said ultrasound system, detecting ultrasound energy reflected from at least two detection points of the subject by irradiating said at least two detection points with the second ultrasound beam while temporally multiplexing said first and second ultrasound beams without mechanical repositioning of said transducer to avoid using another transducer in said ultrasound system,
   d) with a programmable processor, operably cooperated with the ultrasound system, determining, from the detected ultrasound energy, echo data indicative of a target shear wave induced in said subject locally, at the origin region, by said target acoustic radiation force, said target shear wave propagating from said origin region towards said at least two detection points;
   determining, from said echo data, a target shear wave displacement;
   determining, from the echo data, target parameters of the target shear wave,
      said target parameters including at least one of speed and attenuation of the target shear wave;
   calculating a normalized shear wave displacement induced in said subject locally, at the origin region, by a normalized acoustic radiation force formed by irradiating said origin region with said first ultrasound beam under normalization conditions,
      wherein said normalization conditions are defined by having a unit peak intensity of said first ultrasound beam at a boundary of said transducer;

wherein said calculating includes calculating the normalized shear wave displacement $\bar{u}^{sim}(x,x_0)$ according to $$\bar{u}^{sim}(x,x_0)=\int_D \mathcal{G}\,(x-y)\overline{ARF}(y,x_0)dy,$$

wherein $\overline{ARF}(y,x_0)$ is normalized radiation force evaluated at point y with $x_0$ being a position of a focal point of the transducer, G is an elastodynamic Green's function, and a volume integral is computed over the origin region D;
   e) with the ultrasound system, measuring said nonlinear elastic parameter at the origin region of the subject based on a mean ratio of said target shear-wave displacement to said normalized shear wave displacement, said mean ratio $SC(x_0)$ expressed according to a product $$SC(x_0) = \frac{1}{n}\sum_{k=1}^{n} \frac{|u^{obs}(x_k, x_0)|}{|\bar{u}^{sim}(x_k, x_0)|},$$

wherein S is a peak input intensity, $|u^{obs}(x_k,x_0)|$ is a measured peak of the normalized shear wave displacement at a measurement point $x_k$, C is a nonlinearity parameter, and a variable $x_0$ denotes a position of the origin region D and a point in a tissue at which the nonlinearity parameter C is evaluated, k is an index of summation, and n is an upper bound of summation;
   and
   based on the measured nonlinear elastic parameter, spatially differentiating a malignant tissue of the subject from a benign tissue of the subject.

2. The method according to claim 1, wherein said determining echo data includes determining echo data associated with irradiating said subject with the first and second ultrasound beams at least one of which is defined by one or more of
   (i) an amplitude-modulated ultrasound beam and
   (ii) a plurality of ultrasound beams having different frequencies.

3. The method according to claim 2,
   further comprising forming at least one of the first and second ultrasound beams by combining concentric ultrasound beams having different frequencies.

4. The method according to claim 1, wherein said determining echo data includes determining echo data associated with irradiating said origin region with the first ultrasound beam is defined by a first focused amplitude-modulated ultrasound beam and the origin region is coextensive with a focal region of said first ultrasound beam.

5. The method according to claim 1,
   wherein said calculating the normalized shear wave displacement includes calculating the normalized shear wave displacement with the use of one or more of an analytical approximation and the elastodynamic Green's function.

6. The method according to claim 1, further comprising determining, from said mean ratio, a relative value of the nonlinear elastic parameter characterizing the origin region.

7. The method according to claim 1, further comprising making a diagnostic determination about the subject based on a relative value of the nonlinear elastic parameter characterizing the subject at at least one point thereof, said diagnostic determination including differentiating a first material of the subject from a second material of the subject.

8. An ultrasound system configured for determination of a material nonlinearity of a subject and formation of image thereof, said system comprising:

an ultrasound transducer configured
- to generate a first ultrasound beam defining a focal region in the subject,
- to transform said first ultrasound beam into a second ultrasound beam directed to at least one detection point of the subject, said at least one detection point being spatially separated from the focal region in a direction transverse to the first ultrasound beam;
- to temporally multiplex the first and second ultrasound beams without mechanical repositioning of said ultrasound transducer;
- to receive echo data, from the at least one detection point, indicative of an acoustic radiation force formed in said focal region in response to irradiating said focal region with the first ultrasound beam,
- said acoustic radiation force having a component that is non-linear with respect to amplitude of said first ultrasound beam and inducing a shear wave propagating from said focal region outwardly,
- said subject having a nonlinear elastic parameter of a material of the subject;

a computer-readable tangible non-transitory medium with computer program code stored thereon which, when loaded on a data-processing electronic circuitry that is in operable communication with said ultrasound transducer, causes said circuitry
  (i) to determine, from said echo data, target shear wave displacement;
  (ii) to determine, from said echo data, target parameters of a target shear wave, said target parameters including at least one of speed and attenuation of said target shear wave;
  (iii) to calculate a normalized shear wave displacement $\overline{u}^{sim}$ according to $$\overline{u}^{sim}(x,x_0) = \int_D \mathcal{G}(x-y)\overline{ARF}(y,x_0)dy,$$

wherein $\overline{ARF}(y,x_0)$ is normalized radiation force evaluated at point y with $x_0$ being a position of a focal point of the ultrasound transducer, G is an elastodynamic Green's function, and a volume integral is computed over a focal region D, wherein the normalize shear wave displacement is induced in said subject by a normalized acoustic radiation force formed in said focal region by irradiating said focal region with the first ultrasound beam under normalization conditions, wherein said normalization conditions defined by having a unit peak intensity of said first ultrasound beam at a boundary of the ultrasound transducer;

(iv) to determine, from a mean ratio of said target shear-wave displacement to said normalized shear wave displacement, said nonlinear elastic parameter characterizing the focal region of the subject, and to spatially differentiate a malignant tissue of the subject from a benign tissue of the subject from a spatial distribution of said nonlinear elastic parameter;

and a display system, operably connected with said ultrasound transducer, said computer-readable tangible non-transitory medium, and said data-processing electronic circuitry, the display system configured to transform the mean ratio of said target shear wave displacement to said normalized shear wave displacement, determined with the use of said circuitry, into an image representing a spatial distribution of the non-linear elastic parameter across the subject, wherein said mean ratio $SC(x_0)$ is expressed according to a product $$SC(x_0) = \frac{1}{n}\sum_{k=1}^{n}\frac{|u^{obs}(x_k, x_0)|}{|\overline{u}^{sim}(x_k, x_0)|},$$

wherein S is a peak input intensity, $|u^{obs}(x_k,x_0)|$ is a measured peak of the normalized shear wave displacement at a measurement point $x_k$, C is a nonlinearity parameter, and a variable $x_0$ denotes a position of the focal region D and a point in a tissue at which the nonlinearity parameter C is evaluated, and k and n are integer variables over which an operation of summation is being performed.

9. The system according to claim 8, wherein the first ultrasound beam is defined by one or more of an amplitude-modulated ultrasound beam and a plurality of ultrasound beams having different frequencies.

* * * * *

UNITED STATES PATENT AND TRADEMARK OFFICE
CERTIFICATE OF CORRECTION

PATENT NO. : 10,136,876 B2
APPLICATION NO. : 14/038181
DATED : November 27, 2018
INVENTOR(S) : Bojan Guzina et al.

It is certified that error appears in the above-identified patent and that said Letters Patent is hereby corrected as shown below:

In the Specification

Column 4, Line 10, "a" should be --α--.

Signed and Sealed this
Twenty-fifth Day of December, 2018

Andrei Iancu
*Director of the United States Patent and Trademark Office*